United States Patent [19]

Avnir et al.

[11] Patent Number: 5,824,526

[45] Date of Patent: *Oct. 20, 1998

[54] DOPED SOL-GEL GLASSES FOR OBTAINING CHEMICAL INTERACTIONS

[75] Inventors: David Avnir; Michael Ottolenghi; Sergei Braun; Rivka Zusman, all of Jerusalem, Israel

[73] Assignee: YISSUM, Research Development Company of the Hebrew University of Jerusalem, Israel, Jerusalem, Israel

[*] Notice: The term of this patent shall not extend beyond the expiration date of Pat. No. 5,650,311.

[21] Appl. No.: 667,746

[22] Filed: Jun. 21, 1996

Related U.S. Application Data

[63] Continuation of Ser. No. 266,441, Jun. 28, 1994, Pat. No. 5,650,311, which is a continuation of Ser. No. 937,259, Aug. 31, 1992, abandoned, which is a division of Ser. No. 637,873, Jan. 8, 1991, Pat. No. 5,300,564.

[30] Foreign Application Priority Data

Jan. 23, 1990 [IL] Israel .......................................... 93134

[51] Int. Cl.$^6$ ............................... G01N 1/00; A61K 9/50; B01J 13/18
[52] U.S. Cl. ................... 435/176; 252/315.6; 252/408.1; 424/484; 428/402.24; 436/527; 501/12; 514/944; 514/965; 530/811
[58] Field of Search ............................. 252/183.13, 184, 252/315.6, 408.1; 428/402.24; 501/12; 65/21.1; 436/169, 527; 210/498, 500.26; 422/238, 239; 435/176; 424/484; 514/944, 965; 530/811

[56] References Cited

U.S. PATENT DOCUMENTS

| | | | |
|---|---|---|---|
| 2,054,885 | 9/1936 | Schröter | 252/183.13 X |
| 3,930,951 | 1/1976 | Messing | 435/176 |
| 3,954,678 | 5/1976 | Marquisee | 252/62.53 X |
| 3,990,849 | 11/1976 | Lee et al. | 436/169 |
| 4,076,542 | 2/1978 | Deeg et al. | 501/12 X |
| 4,148,689 | 4/1979 | Hino et al. | 435/176 X |
| 4,169,069 | 9/1979 | Unger et al. | 428/402.24 |
| 4,273,865 | 6/1981 | Von Stetten et al. | 435/176 X |
| 4,274,832 | 6/1981 | Wu et al. | 435/11 X |
| 4,349,456 | 9/1982 | Sowman | 428/402.24 X |
| 4,436,823 | 3/1984 | Blumcke et al. | 436/169 |
| 4,686,195 | 8/1987 | Yamane | 501/12 |
| 4,851,373 | 7/1989 | Hench et al. | 501/12 |
| 4,880,851 | 11/1989 | Yamamoto et al. | 428/402.24 X |
| 4,897,468 | 1/1990 | Oka et al. | 530/811 |
| 4,909,938 | 3/1990 | Ford | 210/496 |
| 4,931,362 | 6/1990 | Zsifkovits et al. | 428/402.22 |
| 4,941,993 | 7/1990 | Strehlow et al. | 252/315.6 |
| 5,009,688 | 4/1991 | Nakanishi | 501/12 X |
| 5,076,980 | 12/1991 | Nogues et al. | 501/12 X |
| 5,292,801 | 3/1994 | Avnir et al. | 525/54.1 |
| 5,300,564 | 4/1994 | Avnir et al. | 525/54.1 |
| 5,650,311 | 7/1997 | Avnir et al. | 435/176 |

FOREIGN PATENT DOCUMENTS

1281106 11/1989 Japan .................................. 210/500.26

OTHER PUBLICATIONS

"Inorganic Gels for Immobilization of Biocatalyst: Inclusion of Invertase–Active Whole Cells of Yeast (Saccharomyces Cerevisiac) Into Thin Layers of $SiO_2$ Gel Deposited on Glass Sheets", G. Carturan et al., Journal of Molecular Catalysis, 57 (1989), pp. L13–L16.

"Covalent Immobilization of Proteins and Peptides for Solid–Phase Sequencing Using Prepacked Capillary Columns", Song–Ping Liang, et al., Analytical Biochemistry 188, (1990), pp. 366–373.

"Sol–Gel Science, The Physics and Chemistry of Sol–Gel Processing", C. Jeffrey Brinker, Chapter 3, (Hydrolysis and Condensation II, Silicates), pp. 97–233, (1990).

"Water Consumption During the Early States of the Sol–Gel Tetremethylorthosilicate Polymerization as Probed by Excited State Proton Transfer ", Vered R. Kaufman, et al., Journal of Non–Crystalline Solids 99 (1988), pp. 379–386.

"Structural Changes Along the Sol–Gel–Xerogel Transition in Silica As Probed by Pyrene Excited–State Emission", Vered R. Kaufman, et al., Langmuir 1986, 2, pp. 717–722.

"The Nature of the Silica Cage as Reflected by Spectral Changes and Enhanced Photostability of Trapped Rhodamine 6G", David Avnir et al., J. Phys. Chem., 1984, 88, pp. 5956–5959.

"Production of L–Aspartic Acid by Microbial Cells Entrapped in Polyacrylamide Gels", Ichiro Chibata et al., Methods of Enzymology 44 (XLIV) (1976), pp. 739–746.

"Data on Techniques of Enzyme Immobilization and Bio-affinity Procedures", Professor J.F. Kennedy, Chapter 4, pp. 380–420, (1985).

"Principles of Immobilization of Enzymes", Professor J.F. Kennedy, Chapter 4, 147–207, (1985).

Knobbe et al., "Organic Molecules Entrapped in a Silica Host for Use as Biosensor Probe Materials", SPIE vol. 906, Optical Fibers in Medicine III (1988).

Wiseman: "Outline of Properties of Immobilized Enzymes" and Data on Techniques of Enzyme Immobilization, *Handbook of Enzyme Biotechnology*, $2^{nd}$ Edition., A. Wiseman/ Ellis Horwood Ltd., England (1985) pp. 190, 191 and 402–405.

Carturan et al.: "Inorganic Gels for Immobilization of Bio-catalysts: . . . ", *J. of Molecular Catalysis*, 57 (1989) L13–L16.

*Primary Examiner*—Richard D. Lovering
*Attorney, Agent, or Firm*—Lowe Hauptman Gopstein Gilman & Berner

[57] ABSTRACT

A sol-gel glass doped with one or more reagent that provides chemical interactions with diffusible solutes or components in an adjacent liquid or gas phase. The reagent(s), the solutes or the components can be any organic or inorganic compounds or materials of biological origin, including enzymes. The doped sol-gel glass in various forms is useful as an analytical test, chromatographic medium, sensor, catalyst or biocatalyst, electrode or enzyme electrode, and other detection devices.

11 Claims, 1 Drawing Sheet

DOPED SOL-GEL GLASSES FOR OBTAINING CHEMICAL INTERACTIONS

This application is a continuation of application Ser. No. 08/266,441 filed Jun. 28, 1994, U.S. Pat. No. 5,650,311, which is a continuation of application Ser. No. 07/937,259 filed Aug. 31, 1992, now abandoned, which is a division of application Ser. No. 07/637,873 filed Jan. 8, 1991, which issued as U.S. Pat. No. 5,300,564.

The present invention relates to a method for obtaining an interaction between reagent/s in a solid support and diffusible solutes or components in an adjacent liquid or gas phase, wherein said reagent/s are trapped in sol-gel glass (hereinafter also referred to as doped sol-gel glass) which provides the solid support to the reagent/s.

The method according to the present invention can be applied to a variety of interactions between the doped sol gel glasses and reagent/s in an adjacent liquid or gas phase. The present invention can be useful in a myriad of applications: for quantitative and/or qualitative analyses, for extraction or separation of solutes from liquid solutions, and for many other applications. For example, the above method can be useful for detection of ions by chemical interaction between the ion/s in an aqueous phase and reagents trapped in the "sol-gel" glass, or vice versa, via characteristic "color test" reactions, or other routine detection methods. Another example is utilization of the above method for qualitative and/or quantitative analyses of pollutants.

The method can be applied as well for medical diagnostic purposes e.g. for detecting inorganic ions and/or small organic molecules in blood, urine and other body liquids. Another example, according to the present invention, is a chemical interaction between a substrate/antigen in the liquid phase and an enzyme/antibody trapped in the "sol-gel" glass.

For centuries, inorganic glasses have been prepared by high temperature melting methods. This has imposed a major limitation upon the technological application of glasses: additives were restricted to thermally stable inorganic materials, while precluding the incorporation of labile organic molecules.

A recent major development in material science has been the preparation of inorganic (silica) glasses through the low temperature "sol-gel" synthesis (Brinker, C. J., Scherer, G. W., Sol-Gel Science, Academic Press, San Diego (1990)). An amorphous bond network of the glassy material is prepared by the room-temperature polymerization of suitable monomers, usually metal alkoxides, according to schemes such as:

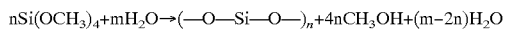

in which water is consumed by

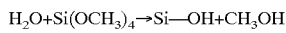

and released by

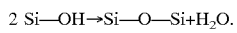

By sol-gel glass one also means the product obtained by a polymerization of metal alkoxide mixtures which bear both hydrolyzable and nonhydrolyzable substituents.

The result of the polymerization is a transparent porous solid (xerogel) with surface areas of up to hundreds m²/gr and by narrow pores (0.5–500 nm).

The low-temperature glass synthesis allows doping inorganic (silica or other) glasses, with essentially any organic molecule. This possibility was used for trapping of e.g. photoactive molecules by adding the compound to the starting mixture at the onset of polymerization (Avnir, D., Levy D., Reisfeld, R., J. Phys. Chem. 88, 5956 (1984)). The compound remained permanently trapped, i.e. non-leachable system have been obtained. These doped sol-gel glasses have been used as photoactive materials, such as:

(a) Dye laser materials;
(b) Thin-film optical filters;
(c) Fluorescent solar collectors;
(d) Photochromic and phosphorescent glasses.

The interaction between the optical properties of trapped molecules and their environment was employed for monitoring the progress of the glass formation sequence: monomer→oligomer→sol→gel→xerogel. This allowed to scrutinize the evolution of such parameters as porosity, water content and degree of (cage) polarity (Kaufman, V. R., Avnir, D., Structural changes Along the Sol-Gel-Xerogel Transitions, Langmuir 2, 717 (1986); Kaufman, V. R., Avnir, D., Pines-Rojanski, D., Huppert, D., Water Consumption During the Early Stages of the Sol-Gel Polymerization, J. Non-Cryst. Solids 99, 379 (1988)).

Sol-gel glasses demonstrate several technologically attractive properties:

(a) the ability to isolate a single doping molecule in an individual cage, even at high concentrations of additive, thus avoiding interfering side photophysical processes and interactions with impurities or photodecomposition products;

(b) thermal and photochemical stability as well as transparency in the U.V. range above 250 nm.

(c) lack of leaching of the trapped compound, simplicity of preparation, and easy technological manipulation allowing production in any desired geometry, including films.

Surprisingly, it was found that molecules trapped in sol gel glasses, may interact with diffusible solutes or components in an adjacent liquid or gas phase in the pore space. Said finding opened a new wide range of applications of doped sol-gel glasses as solid media for chemical interactions.

The present invention relates to a method for obtaining an interaction between one or more reagents in a solid support and diffusible solute/s or component/s in an adjacent liquid or gas phase, wherein said reagent/s are trapped in the sol-gel glass which serves as the solid support. Said reagent/s can be any organic compound, organometallic, or inorganic compound, or any biological material capable of being trapped in the sol-gel glass.

The diffusible solute/s or components can be any organic compound, stable organic radical, organometallic, or inorganic compound or biological material capable to interact with the trapped reagents.

The interaction between the reagent in the solid support and the diffusible solute in the liquid phase or a component in the gas phase can be a chemical interaction such as for analytical tests or chemical reactions. The method according to the present invention can be a specific color test reaction, N.M.R. or E.S.R. analysis, analysis via emission or absorption, luminescence, fluorescence, phosphorescence tests and/or electrochemical tests. The analytical reagent can be a pH indicator, redox reagents or an ion complexant etc.

The chemical interaction according to the present invention can take place between anions or cations in a liquid or gas phase and reagents trapped in the sol gel glass or vice versa. For example the interaction may take place between metal ions and a specific reagents via a characteristic colour-test reaction, as in: (1) the determination of $Fe^{+2}$ cation with o-phenanthrolin, (2) the determination of $Co^{+2}$ with 1-nitroso-2-naphtol, (3) the determination of $Ni^{+2}$ wherein the reagent is dimethylglyoxime, (4) the determination of $SO_4^{-2}$ anion wherein the reagent is sodium rhodizonate and $BaF_2$, or benzoinoxime, (5) the detection of $H^+$ is one of many examples for a pH sensors. The analytical test can be carried out by dipping the doped sol gel glass in the solution and observing the resulting color change.

The above method can be useful for the analysis of ore contents in soil, sea water, and rocks (e.g. uranium).

The sol gel glass according to the present invention can be in any shape suitable for the test. For example it can have the shape of rods, discs, cubes, sieves, powder, or thin films coating conventional glass plates or any other inert solid support. Thus, an electrochemical test according to said invention can be performed by preparing electrodes coated with doped sol gel glass layers. These electrodes may be used for clinical, analytical or industrial purpose, or as biosensors.

It should be emphasized that the method according to the invention can be useful for qualitative and for quantitative analysis.

The method according to the present invention can be applied to detection and analysis of pollutants in soil, in aquatic environments and characteristic water sources (including waste, industrial and municipal sources, lakes and swimming pools) in food, drugs, or in the air. The method may be applied to qualitative and/or quantitative analysis of pollutants. Said pollutants may be for example chlorides, nitrates, phosphates, herbicides, insecticides, inorganic ions and pollutants of organic origin. Detection devices according to this invention can be utilized as a part of continuous monitoring systems.

The present invention can be utilized for extracting or separating molecular solutes from liquid solutions. The doped sol gel glasses can be used according to the present invention for all chromatographic purposes, including liquid, gas and thin layer chromatography. The extraction or separation is performed by passing the solution through columns made from appropriately doped sol gel material. The thin layer chromatography according to this invention can be performed on conventional glass plates, paper or other inert solid support coated with doped sol-gel glass layers.

Medical diagnostic is another application of the present invention. For example, detection of inorganic ions, small organic molecules and other components in blood, urine and other body liquids. The invention can be applied also to the fractionation of body fluids.

The present invention relates, as well, to a method for preparation of bioactive materials (biocatalysts) by entrapment of enzymes in a forming sol-gel glass, which, following polycondensation of suitable monomers, serves as a solid matrix, bonding the enzyme and conveying to it mechanical, chemical and thermal stabilities.

The method, according to the present invention, can be applied to a variety of enzymes or enzyme systems, including co-immobilization of co-factors, organic and inorganic ligands, mono- and polyclonal antibodies, and their detection systems.

The method according to the present invention can be useful in a variety of applications, such as: (a) biochemical reactions and other bioconversions in organic and inorganic solvent solutions, (b) detection or qualitative determination of organic and inorganic molecules, which are substrates of the immobilized enzymes, or inhibitors, or modifiers of enzyme activity, (c) construction of bioelectronic detection devices, including construction of enzymes electrodes and biosensors.

Commercial applications of enzymes require successful immobilization. Immobilization allows reuse of an enzyme, protects it from harsh external conditions, from microbial contamination, and prolongs their useful lifetime. There are probably as many immobilization methods as there are enzymes. This proliferation of techniques reflects the complexity of the biological material and the variety of its uses. Simple inexpensive general techniques, resulting in stable and active enzyme catalyst are still in great demand (Kennedy, J. F. and White, C. A. in "Handbook of Enzyme Biotechnology" (Wiseman, A. ed.), Ellis Horwood Ltd, Chichester, pp. 147–207 (1985)).

An ideal enzyme catalyst should be bound to a mechanically and chemically stable, highly porous carrier. The bond linking the enzyme to the support is required to be stable under the catalyst application conditions to prevent leaching. The strong binding forces also have stabilizing effects on enzyme activity (Martinek, K. and Mozhaev, V. V. Adv. Enzymol. 57, 179, (1985)). The desired immobilization procedure should be simple, mild (non-denaturing) and generally applicable.

Enzymes covalently immobilized on controlled-pore glass beads offer an almost ideal solution to the problems of the support and of the binding force. However the preparation of catalyst by this immobilization technique is neither simple nor generally applicable. The beads are costly, require tedious chemical derivatization procedures, and lack in stability due to the continuous leaching of silica during prolonged usage (Kennedy, J. F. and White, C. A. in "Handbook of Enzyme Biotechnology" (Wiseman, A. ed.), Ellis Horwood Ltd, Chichester, pp. 380–420 (1985)).

The most generally applicable immobilization procedure is a simple entrapment of the enzyme in a forming gel of natural or synthetic polymers. The main shortcoming of this technique is the loss of the enzyme by leakage through a nonuniform net of polymer molecules. Rather weak interactions between the enzyme and the matrix result in a relatively nonrestricted diffusional movement of polypeptide chains. This can be of a benefit, whereas conformational transitions are required for successful catalysis. Otherwise, this diffusional freedom of motion can negatively affect immobilized enzyme stability.

Several properties of the sol-gel glasses make them especially attractive as possible enzyme catalyst supports: (a) the ability to entrap large amounts of additives; (b) the thermal and chemical stability of the matrix; (c) simplicity of preparation with no need of covalent modification; (d) easy technological manipulation and production in any desired geometry, including thin films.

Recently, aggregates of whole yeast cells trapped in thin layers of $SiO_2$ gels deposited on glass sheets were demonstrated to possess invertase activity. Thin films with cell-free invertase preparation were devoid of activity (Carturan, G., Campostrini, R., Dire, S., Scardi V. and de Alteriis, E. J. Mol. Cat., 57, L13, (1989)).

The present invention relates therefore also to a method for obtaining bioactive materials based on an enzyme molecules trapped within the porous structure of a sol-gel glass. The entrapment is achieved by the addition of a cell-free enzyme to a mixture of monomer or monomers at the onset of polycondensation. In addition to the enzyme and monomer(s), the mixture should contain additives ensuring (1) highly porous nature of the forming glass providing minimal diffusional limitations to the binding of the substrate at the catalytic site and to the removal of the product, (2) the stability of the enzyme during the polymerization and its tight binding preventing leaching of the enzyme.

Unexpectedly, we have found (1) that proteins can be trapped within the matrix of a forming sol-gel, (2) that several cell-free enzymes, belonging to various classes: hydrolases, oxidoreductases, lyases etc., can be effectively entrapped in such composite bioactive sol-gel glasses, while retaining high enzymatic activity, (3) that strong binding forces retain the enzyme in the matrix, thus producing a considerable stabilizing effect.

The sol-gel immobilized enzymes may be used as biosensors for hormonal tests or for any industrial purposes, including diagnostic and synthetic purposes. Said enzymes can be doped in sol gel glass layers coated on electrodes for probing any substrate. The enzymatic interaction according to the present invention can be applied also to radioactive tests and also for enzymatic column chromatography (crushed powder sol gel glasses may be used as support for enzymatic column chromatography).

The sol gel glass can be applied, according to the present invention, as active specific membranes allowing selective incorporation of the trapped molecules or ions or any other species.

The abovementioned applications are examples only and do not intend in any way to limit the scope of the invention.

The present invention relates also to the application of doped sol gel glasses according to this invention as well as for the preparation of sol gel glasses and doped sol gel glasses for such applications.

When prepared as thin film the width of the sol gel glass may be from molecular monolayers up to macroscopic layers. Said thin film can be part of multi-layered array of thin films. Said glasses may be supported on an electrode or optical support.

The unique transparency of "sol gel" glasses in the range above 250 nm, makes them highly applicable to quantitative spectrophotometric and spectrofluorimetric tests. Trapping of host molecules is relatively simple and does not require specific synthetic methods such as those associated with covalent linking of reagents to solid supports. Moreover, inherent properties of sol gel glasses such as high surface area, the wide range of available pore sizes and the thin film technology, make them highly attractive for potential applications as solid supports for a variety of reagents.

BRIEF DESCRIPTION OF THE DRAWING

The FIGURE drawing shows various glasses with a reagent trapped therein, both before and after reaction with a component in the liquid phase.

EXAMPLES

A. Preparation of doped "sol-gel" glasses

Figure 1:
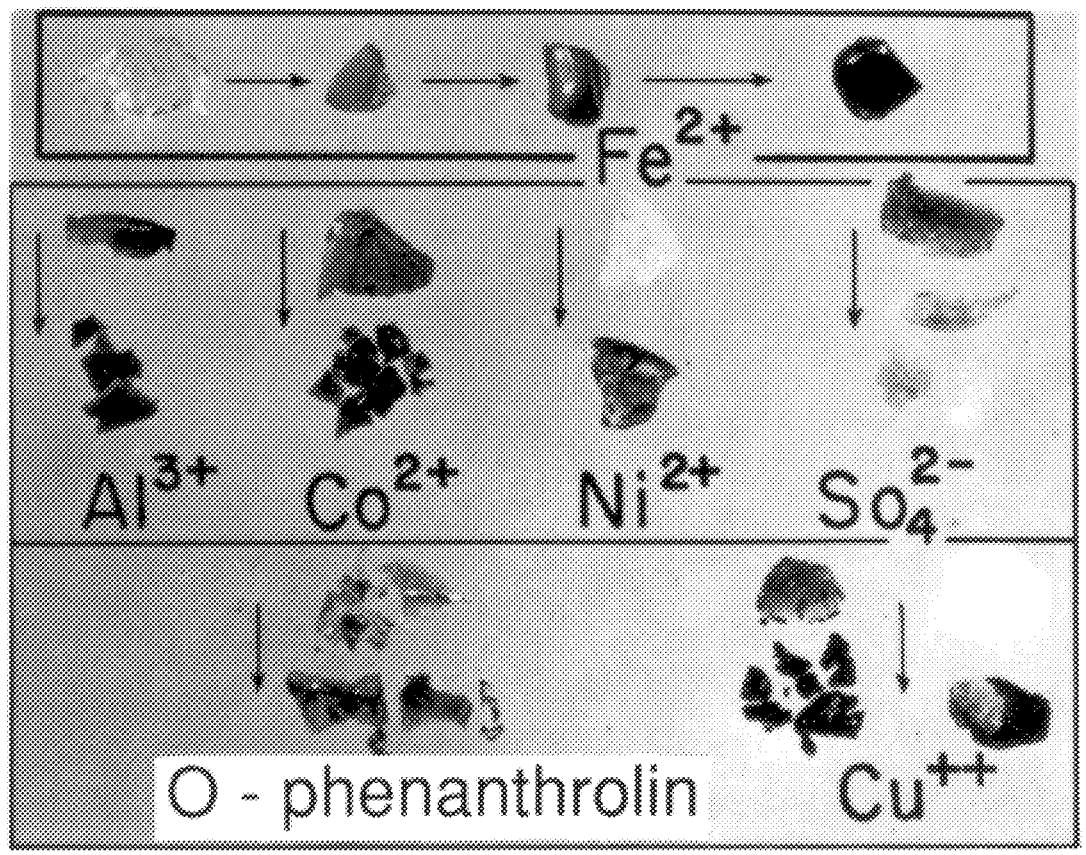

The polycondensation of alkoxysilanes is associated with gelation of the sol, which after drying is densified by a mild heat treatment to form a glass. The properties of the final glass are determined by the chemical and physical conditions during the process of preparation. They depend upon the ratio metal (e.g. silane)/alcohol/water, the alkoxide pH, the presence of a catalyst, the temperature, the drying time and the amounts of organic additives, such as surface active agents.

Pore size and surface area are controlled by addition of acid or base (see Scherer and Brinker, 1990, cited above).

Addition of NaF to the starting (TMOS) solution leads to an increase in average pore size.

1. A standard mixture for preparation of doped "sol-gel" glasses contained TMOS (5 ml) $H_2O$ (2.4 ml) and methanol (6. ml). The appropriate catalyst and the desired reagent were added in the required amounts (water or methanol solutions). Gels were formed within several minutes (base-catalyzed) or several hours (acid-catalyzed). Gelation was carried out at room temperature in glass bottles covered with aluminium foil. The gels were then transferred to an incubator and kept at 37°–45° C. The samples were used after they reached a constant weight (about two weeks). The above procedure yields glass in any desired shape(rods, disks etc.).

2. An alternative technique of preparing sol-gel glasses is based on thin-layer coating of conventional glass supports. A characteristic procedure for the preparation of such thin layers began with a mixture containing methanolic or ethanolic solution of dopant (85 ml), TMOS (10 ml), Triton X-100 (3 g) and 0.03N HCL or 0.01N NaOH (3 ml). After mixing the solution was allowed to stand for 30 min at 25°–35° C. and was then used for coating. Coating was performed by dipping a glass plate into the solution, followed by drying for several minutes at room temperature. The resulting porous coating layer (0.25–0.5 $\mu$m).

B. Representative examples of reactivity of reagents trapped in sol-gel glasses

1. Tests were carried out by the immersion for 5 min of an appropriately doped sol-glass in aqueous solutions containing ions or molecules to be detected. Arrows denote transitions from the reagent-doped glass to the same glass after immersion in the tested solution. The doped glasse≦represent four classes of reactions: (a) a glass-trapped organic reagent with an inorganic cation to be determined in the solution; (b) same with inorganic anions; (c) a glass doped with an inorganic ion, testing a solution containing an organic molecule (reversal of a & b); (d) glass doped with a pH indicator.

Representative examples of color tests are shown in Table 1. Top (left to right): a) Glass doped with 1,10-phenanthrolin after immersion in: b) $10^{-5}M$ $Fe^{2+}$ solution, c) $10^{-4}M$ $Fe^{2+}$, d) $10^{-2}M$ $Fe^{2+}$. Glass was prepared in the presence of the reagent (0.005%) and $5\times10^{-3}M$ NaOH as catalyst in the starting aqueous solution.

Middle: Doped glasses (top) and some glasses after immersion in solutions containing several ions:

a) Reagent for $Al^{3+}$ was quinalyzarin (1,2,5,8-tetrahydroxyanthraquinone). To the starting solution (see above) 2 drops of a solution with the following composition were added: 18 cc methanol containing 0.01 gr of the reagent, 2 cc pyridine and two drops of 0.1N $NH_4OH$. b) Reagent for $Co^{2+}$ was nitroso naphthol. Starting solution contained 0.25% of the reagent and 3 drops of 0.1N HCl as catalyst. c) Reagent for $Ni^{2+}$ was dimethylglyoxime (starting solution, contained 0.25% of the reagent and 3 drops of 0.1N $NH_4OH$ as catalyst. d) Reagent for the $SO_4^{2-}$ anion was sodium rhodizonate & $BaF_2$.

Starting solution contained 0.25% sodium rhodizonate, $3,5\times10^{-3}$ gr. $BaF_2$ and $3\times10^{-3}N$ NaOH.

Bottom left: Glass doped with $Fe^{2+}$ (top, yellow) after immersion in a solution containing o-phenanthrolin (bottom, red). The glass, prepared in the presence of an acid catalyst (a few drops of concentrated HCL), was used before complete drying (container was capped after 3 days).

Bottom right: Two different reagents for the determination of $Cu^{2+}$ (top: glass with reagent, bottom: same after immersion in $Cu^{2+}$ solution). Left: Rubeanic acid as a reagent. Starting solution contained 0.15% of the reagent and 0.25% sodium tartaric in the presence of 0.01N NaOH. Right: Benzoinoxime (Cupron) as reagent. Starting solution contained 0.25% of the reagent with one drop of concentrated HCL. After 3 minutes 3 drops of concentrated $NH_4OH$ were added.

C. Representative examples of bioprocesses involving proteins.

1. Preparation of sol-gel immobilized enzymes.

Enzyme solutions (0.2 ml, 10 mg/ml) in non-buffered water, which may contain various additives were mixed in the cold (4° C.) with either methanol or polyethylene glycol (PEG 400). The concentrations of additives (such as e.g. NaF, NaOH, HCl), the volumes of methanol and PEG 400 were as indicated in the examples below. Tetra-methoxy silane (TMOS, 1 ml) was then added. The tubes containing the reaction mixture were transferred to a shaking water bath at 8° C. The bath was allowed to reach the room temperature during 2–3 h. In samples containing PEG 400, the polymerization was completed in about 3 h.

All the liquid remaining on the top of sol-gel was then removed by suction. In methanol-containing mixtures gelation took place in about 4–5 h. The polymerized sol was allowed to dry for a week at 30° C.

2. Retention of protein by the sol-gel glass.

All the glasses prepared according to example C1 were ground to a size of about 60–100 mesh and packed in 2 ml-columns. The columns were eluted with 0.5M $NH_4HCO_3$ (250 ml), followed by water (250 ml). This cycle was repeated twice. All washing solutions were collected, concentrated by freeze-drying, and assayed for protein content and for respective enzyme activity. It was found that neither significant enzyme activity nor protein could be detected in the eluates.

3. Entrapment of trypsin in sol-gel glasses.

Trypsin (E.C. 3.4.21.4, from bovine pancreas, 11,000 U/mg) was supplied by RAD Chemicals, Rehovot, Israel. Trypsin entrapped in sol-gel was prepared as described in example C1. Assays were performed on the washed glasses at 25° C. at pH 8 using n-benzoyl-L-arginine-4-nitroanilide (3.3 mM) as the substrate. The concentration of NaF in the enzyme solution and the addition of methanol or PEG 400 (ml per ml TMOS) as well as the enzymatic activity of the glass catalyst (expressed in per cent of trypsin activity initially added to the condensation mixture are shown in the following Table:

|  | Trypsin Activity (percent of initial) | | | |
| --- | --- | --- | --- | --- |
|  | MeOH (ml/ml TMOS) | PEG (ml/ml TMOS) | | |
| NaF (mM) | 0.6 | 0.2 | 0.4 | 0.6 |
| 0 | 0.1 | 11.4 | 33.0 | 33.6 |
| 1 | 0.6 | 16.9 | 24.7 | 29.7 |
| 10 | 1.9 | 10.0 | 18.2 | 23.6 |
| 100 | 2.8 | 4.1 | 21.6 | 17.5 |

4. Entrapment of acid phosphatase in sol-gel glasses.

Acid phosphatase (E.C. 3.1.3.2, from wheat germ, 0.45 U/mg) was purchased from Sigma. The acid phosphatase-containing sol-gel glasses were prepared as described in the example C1. The assays were performed on the washed glasses at 25° C. at pH 5.6 using p-nitrophenyl phosphate (6 mM) as the substrate. The activity yield, calculated in percents of enzyme activity used initially for the preparation of glasses, is shown in the following Table:

|  | NaF, mM | | |
| --- | --- | --- | --- |
|  | 1.0 | 3.0 | 10.0 |
| SOLVENT | ACID PHOSPHATASE YIELD, % | | |
| Methanol 0.6 ml/ml | 1.9 | — | 39.2 |
| PEG 400, 0.2 ml/ml | 46.6 | 56.4 | 21.1 |
| PEG 400, 0.4 ml/ml | 39.8 | 41.0 | 46.7 |

5. Thermal stability of immobilized acid phosphatase in different sol-gel glasses.

The acid phosphatase-containing sol-gel glasses (example C4) were incubated at 70° C. in citrate buffer (pH 5.6, 0.1M) for various periods of time (up to 5 min). The activity of acid phosphatase was determined, as described in the legend to Table 1. The half-life time was calculated assuming the 1st order inactivation kinetics. The half-life time of the soluble enzyme at the same conditions was below 0.1 min.

|  | NaF, mM | | |
| --- | --- | --- | --- |
|  | 1.0 | 3.0 | 10.0 |
| SOLVENT | HALF-LIFE TIMES AT 70° C., min | | |
| Methanol 0.6 ml/ml | — | — | 3.9 |
| PEG 400, 0.2 ml/ml | 3.3 | 3.3 | 12.0 |
| PEG 400, 0.4 ml/ml | 3.2 | 3.1 | 3.5 |

6. Entrapment of peroxidase in sol-gel glasses.

Peroxidase (E.C. 1.11.1.7, from horseradish, 200 U/mg) was obtained from Sigma. Sol-gels doped with peroxidase were prepared as shown in the example C1. All the glasses prepared with the addition of PEG 400 were active, although it was not possible to determine the extent of their activity quantitatively, since the dye formed by oxidation of several substrates was adsorbed strongly in the glass. Semi-quantitative comparison of the dye stain shortly after the addition of the assay mixture indicated improved activity yields at higher concentrations of PEG 400. In contrast to trypsin and catalase, sol-gel glasses made at elevated concentrations of NaF were more active. Glasses prepared in methanol-containing mixtures were devoid of peroxidase activity.

7. Entrapment of trypsin in sol-gel glasses.

Trypsin solution (1.0 ml, 2 mg/ml) in non-buffered water was mixed with either 20 mM NaF (0.1 ml) or the same volume of water, and with one of the following: (1) methanol, (2) polyethylene glycol solution (PEG 6000, 20% w/vol in water), or (3) glycerol solution (75% w/vol in water). The mixture was cooled to 4° C. Tetra-methoxy silane (TMOS, 1 ml) was then added. The tubes containing the reaction mixture were transferred to a shaking water bath and allowed to reach the room temperature. The polymerized sol was allowed to dry for a week at 30° C. The resulting glasses were treated as described (example C2). Trypsin activity of the trypsin-doped sol-gel glasses expressed as the yield of activity used for the preparation of the catalyst is presented in the following Table.

|  | TRYPSIN ACTIVITY, % of initial | |
| --- | --- | --- |
| ADDITIVES | +NaF | −NaF |
| Methanol | 17.2 | 26.8 |
| PEG 6000, | 51.3 | 46.1 |
| Glycerol | 82.0 | 38.1 |

8. Entrapment of aspartase in sol-gel glasses.

*Escherichia coli* cells (ATCC 11303) were cultured as described (Chibata, I, Tosa, T., and Sato, T. Meth. Enzymol.

44, 739–746 (1976)). Saline-washed cells (4 g wet weight) were suspended in water (2ml) and disrupted by sonication. The homogenate was cleared by centrifugation (10,000×g, 30 min, 4° C.) and used for the preparation of sol-gel glasses. The homogenate (0.5 ml) was mixed with NaF solution (0.2 ml) at the concentrations indicated in the Table below. Methanol (0.6 ml) or PEG 400 (0.2 ml) was then added followed by TMOS (1 ml). All the additions were made at 4° C. The resulting sol was kept overnight at room temperature and then washed with an excess of 50 mM phosphate buffer pH 7. Aspartase activity was measured and expressed in $\mu$moles/min/g cells (wet weight). The results are presented in the Table. For comparison the polyacrylamide gel-entrapped whole cells from the same batch, prepared according to Chibata (1976), possessed aspartase activity of 133 $\mu$moles/min/g cells.

| NaF solution mM | Aspartase Activity, $\mu$mole/min/g cells | |
|---|---|---|
| | MeOH (ml/ml TMOS) 0.6 | PEG (ml/ml TMOS) 0.2 |
| 0 | 105.0 | 79.0 |
| 1 | 15.8 | 127.7 |
| 100 | 64.5 | 39.8 |

9. Preparation of protein-doped glasses by NaOH catalyzed polycondensation. Immobilization of alkaline phosphatase.

A mixture of tetra-methoxy silane (TMOS, 5 ml), methanol (6 ml) and 1 mM NaOH in methanol (0.1 ml) was cooled to −20° C. and mixed with an ice-cold solution (0.9 ml) of alkaline phosphatase (ALP, E.C. 3.1.3.1 from bovine intestinal mucosa, Type I-S, 8.5 U/mg, Sigma Chem. Co) containing 1.5 mg of the enzyme. A cloudy mixture was allowed to reach room temperature under stirring. The resulting viscous opaque material was kept for 10 days at 37° C. During this time the glass formation was completed and it reached a constant weight. The glass was ground and washed as described in the example C2. The enzyme activity was determined in NaOH-glycine buffer (40 mM, pH 9.5) at 25° C. using p-nitrophenyl phosphate as the substrate. The yield of the alkaline phosphatase activity after immobilization was estimated at about 30%. The half-life time of the immobilized enzyme at 70° C. (pH 9.0) was 4.7 min, as compared to 2.6 min for the soluble ALP at the same conditions.

10. Immobilization of chitinase

The glass trapped enzyme was prepared by adding 1.0 ml of the enzyme chitinase (EC 3.2.1.14, cloned from *Serracia marcensens* and expressed in *E. coli,* 200 units) in the phosphate buffer (10 mM, pH 6.3), to a solution obtained by stirring 3.0 ml methanol and 2. ml TMOS for 15 minutes.

11. Antibody reactions

Interleukin-2 receptor (IL-2R) is the protein that mediates the action of interleukin-2 (IL-2), an immune system growth hormone. Levels of soluble IL-2R have been shown to be elevated in a number of pathological conditions, and may thus be of significant prognostic value. We have used an Anti-IL-2R monoclonal antibody, trapped in a sol-gel glass, to determine IL-2R, using a sandwich immuno assay test (cell-free Interleukin-2 Receptor CK 1020, 96 Test kit, T Cell Sciences, Inc., Cambridge, Mass., USA). Trapping of Anti-IL-2R monoclonal antibody in a "sol-gel" glass was carried out with a starting solution composed of methanol (3 ml), TMOS (2.5 ml), 6 mM phosphate buffered saline (PBS, 0.25 ml) and Anti-IL-2R antibody (0.25 ml, from the kit). After stirring for 50 min. the sample was allowed to stand for 5 days at 27° C.

The resulting glass (4 mg, 0.4% of the total amount) was crushed and washed three times with 350 $\mu$l of the "washing solution" from the kit (0.2 ml surfactant in 200 ml PBS). To this solution 100 $\mu$l the "sample diluent" (buffered serum protein) and 50 $\mu$l of the human IL-2R standard "solution" were added and mixed for 15 sec, followed by covering and incubating for 2 hours at 37° C. After three washings, 100 ml peroxidase- conjugated Anti-IL-2R antibody solution was added and incubated at 37° C. for 2 hours. After three washings with the "washing solution", 100 $\mu$g of o-phenylenediamine dissolved in a "substrate diluent" (buffered $H_2O_2$) were added and incubated for 20 min at room temperature. An absorbance $OD_{490}$=0.93 was recorded, compared to $OD_{490}$=0.357 obtained with the above commercial kit, with a similar amount of Anti-IL-2R monoclonal antibody absorbed into polystyrene microtiter wells.

We claim:

1. A reactive sol-gel comprising a porous solid gel containing a chemically reactive cell-free dopant of biological origin trapped therein and formed by non-denaturing polymerization of at least one monomer of the formula $M(R)_n(P)_m$ and selected from the group consisting of metal alkoxides, semi-metal alkoxides, metal esters and semi-metal esters, wherein M is a metallic or semi-metallic element, R is a hydrolyzable substituent, n is an integer of 2 to about 6, P is a non-polymerizable substituent and m is an integer of 1 to about 6, in the presence of said dopant, said polymerization including a gelling step conducted at not greater than about room temperature, and the dopant being chemically reactive after preparation of the gel.

2. A reactive sol-gel as defined by claim 1, wherein the porous solid gel is in the form of a rod, a disc, a cube, a sieve, a powder, a thin film or an array of thin films.

3. A reactive sol-gel as defined by claim 2, wherein the porous solid gel is a thin film in the form of a molecular monolayer.

4. A reactive sol-gel as defined by claim 2, wherein the porous solid gel is a thin film in the form of a macroscopic layer.

5. A reactive sol-gel as defined by claim 2, wherein the porous solid gel is a thin film and is supported on a solid support including an optical material.

6. A reactive sol-gel as defined by claim 1, wherein the porous gel is in the form of thin sieves.

7. A reactive sol-gel as defined by claim 1, wherein at least two dopants are trapped in the porous solid gel and wherein the at least two dopants are reactive after preparation of the solid gel.

8. A reactive sol-gel as defined by claim 1, wherein the distribution of dopant in the gel is nonhomogeneous and follows a predetermined gradient.

9. A reactive sol-gel as defined by claim 1, wherein the cell-free dopant of biological origin is a protein.

10. A reactive sol-gel as defined by claim 9, wherein the cell-free dopant is selected from the group consisting of enzymes, monoclonal antibodies and polyclonal antibodies.

11. A reactive sol-gel as defined by claim 10, wherein the cell-free dopant is an enzyme.

* * * * *